United States Patent [19]

McGinnis

[11] Patent Number: 4,907,584
[45] Date of Patent: Mar. 13, 1990

[54] RESPIRATORY MASK

[76] Inventor: Gerald E. McGinnis, 131 Kelvington Dr., Monroeville, Pa. 15146

[21] Appl. No.: 163,562

[22] Filed: Mar. 3, 1988

[51] Int. Cl.⁴ .............................................. A62B 7/00
[52] U.S. Cl. .......................... 128/206.24; 128/206.28
[58] Field of Search ....................... 128/205.13, 205.18, 128/205.22, 205.25, 206.21, 206.24, 206.25, 206.26, 206.27, 206.28, 207.13, 206.23, 206.12, 206.14, 206.16, 206.15, 207.12, 206.17; 2/6, 410, 411, 414, 424, 428

[56] References Cited

U.S. PATENT DOCUMENTS

| | | | |
|---|---|---|---|
| 2,199,231 | 4/1940 | Schwartz | 128/206.17 |
| 2,313,999 | 3/1943 | Kreiselman | 128/206.26 |
| 2,875,757 | 3/1959 | Galleher, Jr. | 128/206.26 |
| 2,939,458 | 6/1960 | Lundquist | 128/206.24 |
| 3,330,274 | 7/1967 | Bennett | 128/206.26 |
| 3,908,648 | 9/1975 | McCosker | 128/206.17 |
| 3,918,448 | 11/1975 | McCosker | 128/206.17 |
| 4,020,507 | 5/1977 | Morton | 2/411 |
| 4,024,458 | 5/1977 | Lamb | 2/414 |
| 4,044,399 | 8/1977 | Morton | 2/414 |
| 4,167,185 | 9/1979 | Lewis | 128/206.24 |

Primary Examiner—Edgar S. Burr
Assistant Examiner—Kimberly L. Asher
Attorney, Agent, or Firm—Carothers & Carothers

[57] ABSTRACT

A respiratory mask having a flexible seal that encompasses a space which is formed and adapted to receive nasal or nasal and oral portions of a user's face, the mask also having a rigid support extending continuously adjacent the perimeter of the flexible seal to support a portion thereof against radially outward deformation under the influence of internal pressure within the space encompassed thereby, while permitting a continuously extending perimeteral portion of the flexible seal to resiliently deform against the facial structure of the user to form a surface seal in engagement therewith, the degree of such deformation of the flexible seal being limited by insertion of selected spacers from a family of differently sized spacers intermediate the mask and the face of the user to thereby limit the minimum spacing that may be established between the mask and the face of the user, and to thereby accommodate adjustment of the seal profile to the user's face.

21 Claims, 2 Drawing Sheets

RESPIRATORY MASK

BACKGROUND OF THE INVENTION

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

The prior art of such masks includes U.S. Pat. Nos. 2,939,458; 2,855,924; 2,166,164; 2,706,983; 4,167,185; and 4,414,973. Additional prior art includes British patent specification 8,372,50 and Italian patent 321483.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

The prior are includes at least two types of respiratory face masks for the types of applications mentioned above. The most common type of mask incorporates a smooth sealing surface extending around the periphery of the mask and exhibiting a generally uniform (i.e., predetermined or fixed) seal surface contour which is intended to be effective to seal against the user's face when force is applied to the mask with the smooth sealing surface in confronting engagement with the user's face. The sealing surface may consist of an air or fluid filled cushion, or it may simply be a molded or formed surface of a resilient seal element made of an elastomer such as plastic or rubber. Such masks have performed well when the fit is good between the contours of the seal surface and the corresponding contours of the user's face. However, if the seal fit is not good, there will be gaps in the seal-to-face interface and excessive force will be required to form the seal member and thereby attain a satisfactory seal in those areas where the gaps occur. Such excessive force is unacceptable as it produces high pressure points elsewhere on the face of the user where the mask seal contour is forceably deformed against the face to conform to the user's facial contours. This will produce considerable user discomfort anywhere the applied force exceeds the local perfusion pressure, which is the pressure that is sufficient to cut off surface blood flow. Ideally, contact forces should be limited between the mask and the user's face to avoid exceeding the local perfusion pressure even at points where the mask seal must deform considerably.

The problem of seal contact force exceeding desirable limits is even more pronounced when the positive pressure of the gas being supplied is relatively high or is cyclical to high levels. Since the mask seals by virtue of confronting contact between the mask seal and the user's face, the mask must be held gainst the face with a force sufficient to seal against leakage of the peak pressure of the supplied gas. Thus, for conventional masks, when the supply pressure is high, headstraps or other mask restraints must be tightly fastened. This produces high localized pressure on the face, not only in the zone of the mask seal but at various locations along the extent of the retention straps as well. This too will result in severe discomfort for the user after only a brief time. Even in the absence of excessive localized pressure points, the tight mask and headstraps often may become extremely uncomfortable and user discomfort may well cause discontinued cooperation with the regimen.

A second type of mask, which has been used with a measure of success, particularly in aircraft and rescue applications, incorporates a flap seal of thin material so positioned about the periphery of the mask as to provide a self-sealing action against the face of the user when positive pressure is applied within the mask. With this type of sealing action, the forces which serve to hold the mask in confronting engagement on the face of the user are much lower than with the first type of mask described above. If the flap seal is capable of conforming to the contours of the user's face without forming leak paths, the mask can be used with retention straps which exert little or no net force to push the mask against the user's face. Thus, the overall sensation of constraint and confinement is dramatically reduced for the user. Such a mask, when properly adjusted, can be adapted to any positive internal mask pressure. The sealing flap will be self-sealing as long as there is no looseness in the strapping arrangement which would allow the mask to move away from the face further than the reach of the sealing flap when subjected to internal pressure.

Among the potential limitations of the second described masked type are two of note. First, the sealing flap seals by laying flat against the user's face throughout its length. This action requires a close match between the contours of the face and those of the seal. If the match is not good, the seal will be ineffective. Secondly, the normal response of one applying the mask to a user's face is to push the mask harder against the user's face if the mask does not seal. With the typical flap seal-type mask, increasing contact pressure against the user's face will not help to form an effective seal if the flap seal does not initially fit well to the facial contours. It may, however, lead to patient discomfort and other problems as described above.

Further regarding the above-described second mask type, some of the principal problems one encounters when trying to apply the self-sealing flap concept to the design of the respiratory mask are related to the location of relative low points and high points in the facial contours of the user relative to the shape or contour of the flap seal surface. If the seal surface does not contact the user's face at the relative lower points, then excessive gas leakage will occur thus preventing sufficient internal gas pressure to develop to activate the sealing action of the seal flap at the low points. In the prior art, this problem has been solved for some applications by providing a variety of masks with differing seal flap shapes, sizes and contours. For example, for aircraft breathing masks, especially where expense is not a critical factor, wide variety of mask shapes and sizes may be provided to give the individual users an opportunity to find a mask offering good fit. In other breathing mask applications such as clinical use, where economic considerations may dictate a mask having the capability to accommodate a wide variety of facial sizes and contours, prior flap type seal structures have not generally been able to provide the requisite versatility.

A related problem with flap seal mask structures concerns the high points of the user's face, where the seal flap may tend to distort or collapse and fold in on itself, thus creating a channel for gas leakage, when pressure is applied in order to effect a seal at adjacent relative low points on the user's face. Even where the section thickness of the seal flap is very limited, and the material is very soft and flexible, the internal gas pressure cannot overcome some such seal flap distortion to provide the desired self-sealing.

It is also known to provide the above-described flap seal type mask with integrally molded structural elements to allow for adaptation of the mask seal to a wide variety of facial shapes and contours. More specifically, it is known to provide properly positioned, resiliently deformable upstanding ribs or similar structural means, preferably located internal of the flap seal and integral therewith, to maintain the flap seal in the proper positional relationship with respect to the face of the user even when the seal and associated ribs are resiliently deformed, so that the positive internal mask pressure will provide the requisite self sealing characteristic. This allows a single mask structure to be adapted to a wide variety of facial contours whereby only a few different masks are required to service a wide range of facial contours normally encountered. In theory the self-sealing flap arrangement allows retention strapping to be used without application of high retention forces against the face or about the head of the user. However, many emergency medical technicians have little if any practical experience or training in the proper use of such masks. As a result, the mask straping may often be drawn too tightly and unnecessarily cause considerable patient discomfort. Soft strapping material preferably is utilized with such masks, so that a comfortable sealing action of the seal flap can be achieved and high user tolerance is realized for extended periods. However, even this expedient will not alleviate the discomfort of tightly drawn strapping.

The applicant herein has been a part to prior development of a mask generally of the above-characterized type and including a generally annular seal comprised of a peripheral sidewall having an inturned flexible flap seal adjacent a free end thereof, with the inturned seal being configured for confronting sealing engagement with a user's face as above described. Spaced about the peripheral seal wall are plural, upstanding, flexible ribs which serve to support the peripheral wall and an inturned portion of the seal member located generally outward of the face-engaging surface portion of the seal flap. The described seal structure is intended to permit the flap seal and peripheral sidewall to distort without experiencing any mode of seal defeating deformation such as crimping, buckling, folding or other modes of collapse. In this seal structure, the structural support ribs are located and configured in a manner to provide adequate seal flap support where seal deformation is not required (i.e., at the "low" points of the contours of the user's face) and to resiliently deform in a manner to permit easy and uniform distortion of the seal flap in those areas where distortion is necessary to accommodate "high" points on the contours of the user's face. This above described mask seal structure is considered to be part of the prior art.

BRIEF SUMMARY OF THE INVENTION

The present invention contemplates improvements to provide enhanced effectiveness for a mask of the above characterized second type, such as the mask with flap seal supported by resiliently deformable ribs as described immediately above, with a novel system of spacers for improved ease of retention strap adjustment. More specifically, the invention pertains to a mask having a body member from which there extends a generally annular seal body which projects outwardly of the mask body to a free end portion that includes an inturned seal flap portion. A rigid, contoured perimeter wall forming a support member or barrier encompasses the flexible seal member to support the same against radially outward bulging when subjected to internal gas pressure. The perimeter barrier projects outwardly of the mask body, snugly encompassing the seal member. Furthermore, the outermost extent of the rigid barrier or support member is contoured with portions thereof projecting outwardly of the mask body to a greater extent compared to other portions which project outwardly to a lesser extent, in accordance with the resilient deformation requirements that are imposed on the flexible seal in applying the mask to the face of a user. Generally, the greatest outward projection of the rigid barrier occurs adjacent the laterally opposed sides of a user's nose, for example, in a nasal mask, whereas lesser outward projections occur where the rigid barrier crosses the upper lip and the bridge of the nose.

As noted above, the invention also contemplates a system of spacers for positioning a mask, such as that above described or others, with respect to the face of a user to afford the most effective seal in use. One embodiment of the positioning system contemplated a family of differently sized spacers, each of which is adapted to be carried by the mask by attachment thereof to the mask body in a manner to prescribe a predeterminable standoff distance between the mask and the user's face. Alternative embodiments of the spacing system include inflatable balloon-like spacers which are differentially inflated to provide selected spacing magnitudes, or continuously mechanically adjustable spacers such as a threaded screw spacer apparatus. The spacers permit the mask to be easily positioned with respect to the user's face with the standoff distance imposed by a selected spacer (or spacer adjustment) dictating the degree of initial seal flap deformation which can occur in the process of applying the mask in the user's face. Preferably, for a nasal mask, the spacers would determine a minimum spacing between the mask body and the user's face in the area just above the bridge of the nose. For any of a variety of such spacers, the standoff between the mask body and the user's face would be otherwise determined through support of the mask by other portions of the flap seal, most notably those portions adjacent to the highest points on the perimeter of the rigid barrier contour. In these areas, the barrier provides additional support to the flap seal member (and integral ribs, if provided). The effect of the invention, as described, is to provide enhanced ease of application of a flexible flap seal type nasal mask to the face of a user with enhanced reliability of sealing and improved user comfort.

It is accordingly one general object of the invention to provide a novel and improved respiratory face mask.

A more specific object of the invention is to provide a novel and improved seal assembly for a respiratory face mask.

Another object of the invention is to provide a respiratory face mask with a flap seal structure which includes an encompassing rigid barrier which extends continuously about the lateral perimeter of a flexible seal member and extends outwardly of the mask throughout its entire extent, the outermost extent of the rigid barrier forming a contoured periphery having respective high and low points.

A further object of the invention is to provide a respiratory mask system including spacer means which is utilized in conjunction with the mask to define a selectively variable minimum standoff distance between the mask body and the user's face to thereby define the degree of initial contact deformation between the flexible seal and the user's face, with different spacing magnitudes being selected depending upon the contours of the user's face, and the standoff distance which is perceived to be most desirable to achieve effective and comfortable sealing with the facial contours of any given user.

These and other objects and further advantages of the invention will be more clearly understood on consideration of the following detailed description and the accompanying drawings, in which.

Figure 1:
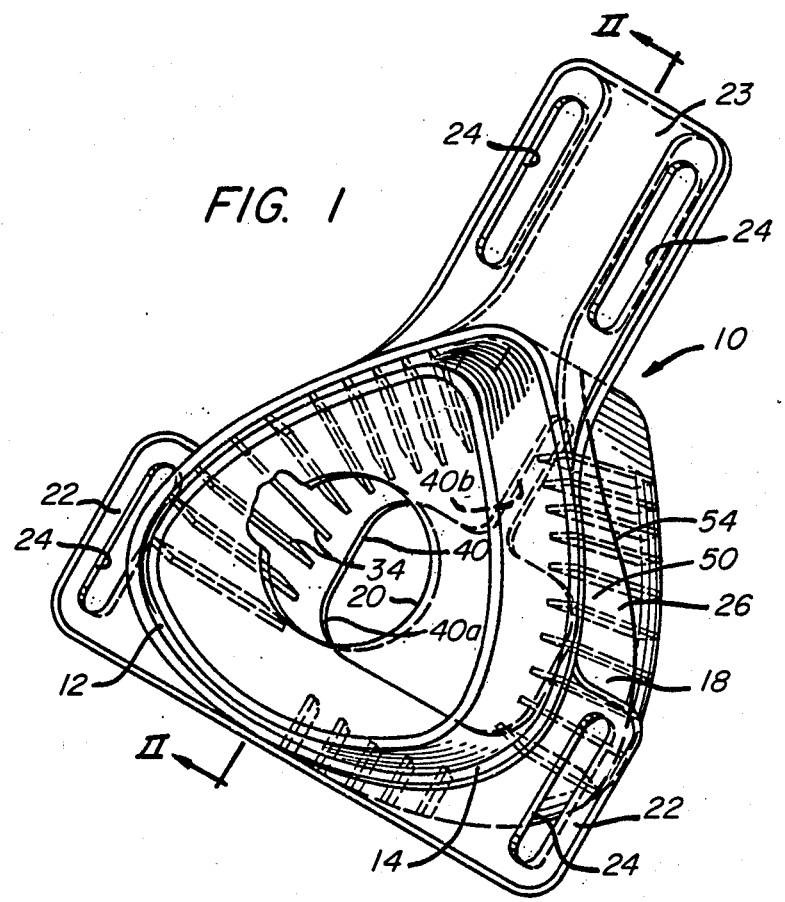
FIG. 1 is a perspective view, partially broken away, of a respiratory mask according to the instant invention.
Figure 2:
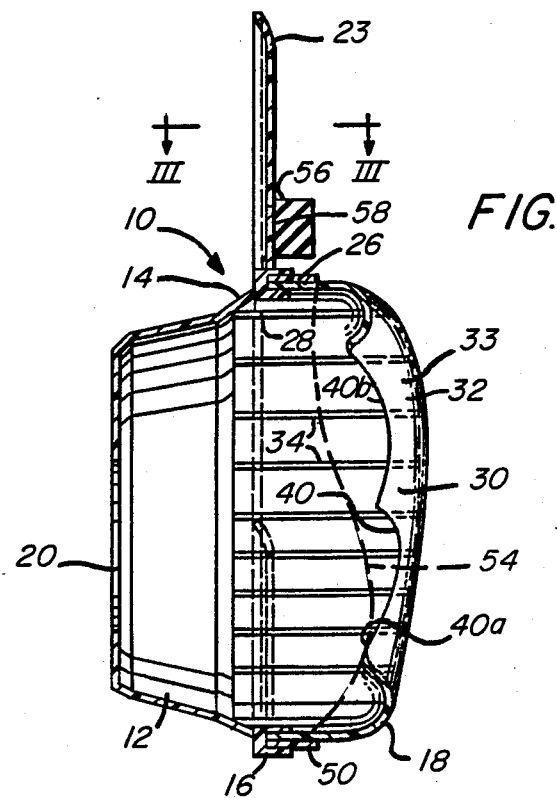
FIG. 2 is a vertical section taken on line II—II of FIG. 1.

There is generally indicated at 10 in FIGS. 1 and 2 a respiratory mask constructed according to one presently preferred embodiment of the instant invention and including a shell or body portion 12 which is preferably, but not necessarily, a generally rigid, formed structural shell having an open side 14 that defines an annular flange portion 16 to which a flexible, resilient, unitary seal member 18 is affixed.

Shell 12 also defines an opening 20 or other suitable means for connecting mask 10 to a supply of gas for nasal administration of the gas to a user. The mask shown thus is a nasal mask or half mask, although it is to be understood that the invention contemplates a full face mask which covers both the nasal and oral openings of the user, or other such known or heretofore unknown mask configurations. Shell 12 further includes two laterally projecting strap retaining tabs 22 and an upwardly projecting strap retaining tab 23, each having suitable elongated apertures 24 which receive and retain suitable conventional retention straps (not shown) for retaining the mask 10 with respect to the face of a user.

Figure 4:
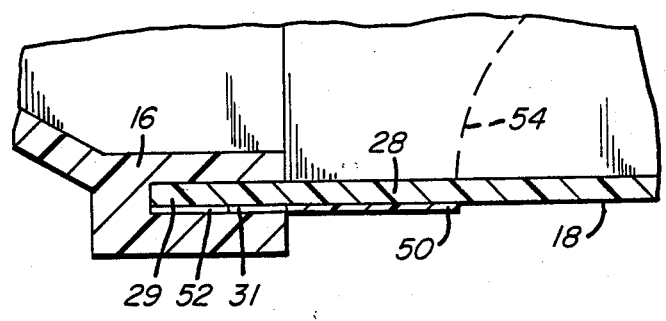
FIG. 4 is an enlarged fragmentary portion of FIG. 2.

Seal 18 includes a thin section, solid flexible, peripheral wall portion 26 as shown in FIGS. 2 and 4 having a base or inner end 28 which is fixedly and sealingly retained with respect to flange 16 as shown in FIG. 4, and from which it will be seen that a peripheral retention portion 29 of inner end portion 28 is received within an annular groove 31 formed in flange 16. The retention end 29 preferably is retained within groove 31 by any such suitable means as an adhesive substance, or a friction or interlocking fit of retention portion 29 within groove 31.

Adjacent the opposed or outer end 33 of peripheral wall portion 26 is a generally annular, inturned seal flap 30 which is integral with wall portion 26 and projects radially inwardly thereof to form a contoured sealing surface 32 for confronting, sealing engagement with a user's face. The contour of seal surface 32 approximates the surface contour of a user's facial structure in the area of the bridge of the nose, the adjacent cheek structure, the area intermediate the nose and the upper lip, and the intervening areas contiguous to these. Accordingly, the radially innermost extent of seal flap 30 forms an opening 40 having an enlarged lower portion 40a and an upwardly extending narrow slot-like portion 40b to receive the nose of a user.

For a full face mask, the seal flap would additionally be contoured to accommodate the user's cheek and chin structure, and contiguous intervening zones. In either case, variation in user facial structure, especially in the area of the bridge of the nose, and in the chin-to-cheek proportions, makes seal flexibility necessary to accommodate the many different facial contours likely to be encountered. However, seal flexibility alone will not provide the requisite accommodation due to the tendency of flexible seals, upon occurrence of differential distortion therein due to the force of mask application and gas pressure force, to crimp, fold or buckle rather than deforming in uniform fashion to follow the facial contours encountered. To provide uniform deformation, the seal member 18 is provided with a plurality of upstanding ribs 34 (FIGS. 1, 2 and 5) which are spaced circumferentially about and integral with the interior periphery of peripheral wall portion 26. The ribs 34 project radially inwardly of wall portion 26 in the same direction as the inward projection of inturned seal flap 30, and their length extends intermediate base ends 28 of the respective ribs and the seal flap 30 of seal member 18.

Figure 5:
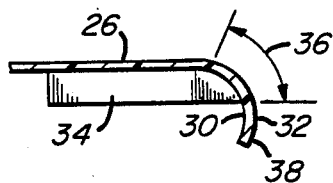
FIG. 5 is a detailed view of a fragmentary portion of the mask of FIG. 1.

As shown in FIG. 5, the ends of ribs 34 adjacent to seal flap 30 preferably are integral with the contiguous portions of seal flap 30 in a zone of transition 36 which connects peripheral wall portion 26 with seal flap 30. Also preferably, the contact surface portion 38 of seal surface 32 extends transversely inward of the innermost extent of the adjacent ribs 34.

The support of seal flap 30 provided by ribs 34 prevents crimping, folding, buckling and other modes of undesirable distortion of seal flap 32 upon application of the mask to a user's face. More specifically, when the mask is first applied to a user, the high points of the facial contours (relative to the mask seal contour) will engage the seal surface 32 first while gaps remain between the seal surface 32 and the relative low points of the user's facial contours. As additional force is applied to close the remaining gaps, the supporting ribs 34 which coincide with the first engaged high points on the user's facial contours will deform by folding laterally while others of ribs 34, not subjected to sufficient force to be deformed, will remain erect or undeformed. This will serve to accommodate deformation of seal surface 32 in a uniform manner to a contour or configuration closely following the confronting contours of the user's face. The stiffness of undeformed ones of ribs 34 adjacent to deformed ones of ribs 34 provides sufficient support to sustain a degree of stretching of the seal flap 32 between the adjacent ribs, thus providing a uniform seal flap contour which follows the contour of the user's face as the ribs 34 are selectively deformed or remain undeformed according to the location of the high and low zones of the facial contours encountered. An improved sealing effect is therefore achieved without application of undue force to maintain the seal engagement with the user's face and without need of a large variety of masks to accommodate the many facial contour variations one might encounter. Of course, the above description of the features of a flap seal for a nasal mask in accordance with my invention is generally applicable also to a full face mask.

As has been noted hereinabove, the concept of internal, upstanding and resiliently deformable ribs included in the structure of a resiliently deformable face seal portion of a respiratory mask, such as the structure described immediately hereinabove, is admitted prior art; however, it is believed that such structure in combination with further novel structure described hereinbelow constitutes one aspect of my patentable invention, and that the hereinbelow described structural features taken in isolation, that is independently of the above described rib structures and independently of each other, are further aspects of my patentable invention.

Accordingly, my novel mask structure further comprises an upstanding, rigid, perimeteral barrier 50 which closely encompasses seal member 18 to provide rigid support for the same throughout a peripheral portion thereof projecting outwardly from flange 16. Thus as shown in FIG. 4, barrier 50 includes a plurality of tabs 52 which project therefrom in a common direction for insertion into the groove 31 adjacent to seal retention portion 29. The tabs 52 serve to retain barrier 50 in encompassing relationship about the perimeter of seal member 18 to provide additional support therefor over and above that provided by ribs 34 or any other supporting structure which might be provided. Barrier 50 projects outwardly of flange 16 to terminate in a contoured outermost end portion 54 which is of varying height at different positions about the perimeter of seal member 18. For example, adjacent the uppermost portion of seal member 18, being that portion adapted to reside adjacent the bridge of a user's nose, the projection of barrier 50 to outermost end 54 is comparatively small, the extent of projection increasing gradually for portions of barrier 50 closer to the lower, laterally opposed portions of seal 18 which are adapted to reside adjacent the cheek structure of the user's face. From these laterally opposed locations, moving toward the lower most part of the mask 10, the outermost extent of barrier end portion 54 is reduced again to reach a lesser extension adjacent that portion of seal member 18 which is adapted to confront the area of a user's face intermediate the nose and the upper lip.

This contoured barrier structure 50 provides for enhanced support of seal member 18 for more uniform and reliable deformation thereof upon application of the mask to user's face. The contoured barrier structure also supports the flexible seal sidewalls against internal gas pressure exerting radially outward force thereon. Specifically in this latter regard, lateral bulging of the seal sidewalls under internal pressure could disturb the seal surface configuration and/or interfere with proper deformation of the seal member which is required to conform the same closely to the facial contours of the user. Because the perimeteral barrier is contoured as above described, the nature of internal pressure containment or resistance to radial bulging differs about the perimeter of the seal member sidewalls in a manner which is conducive to more uniform and reliable seal performance. Specifically, in this regard, it is noted that the contour of the barrier member 50 follows the natural or innate contour of the seal surface relatively closely throughout the region from the laterally opposed side portions of the seal member across the lowermost regions thereof. By contrast, from the laterally opposed side portions to the uppermost part of the seal member, a progressively greater extent of the seal member side walls extend beyond the outermost extent 54 of barrier 50, for example as shown in clearly in FIG. 1. In these regions, therefore, a greater extent of the seal member side wall is unsupported by the rigid barrier 50. This allows for a greter range of seal member deformation in the areas across the bridge of the user's nose, and in contiguous zones adjacent the opposed sides of the user's nose.

Figure 3:
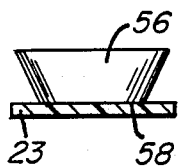
FIG. 3 is a fragmentary sectional view taken on line III—III of FIG. 2.
Figure 6:
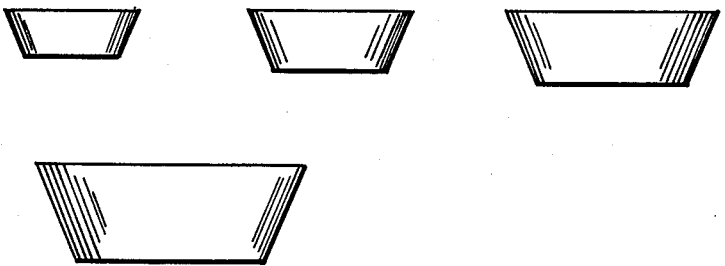
FIG. 6 is an elevational view of one spacing means of the present invention, shown as a family of spacers.
Figure 7:
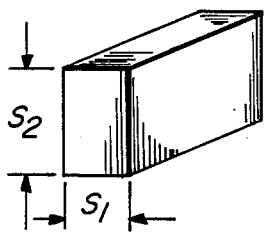
FIG. 7 is a perspective view of an alternative spacer embodiment.

A further aspect of my novel face mask pertains to the provision of a spacer means which preferably is carried by a portion of mask 10 for use in defining a predeterminable, minimum standoff distance between selected portions of the mask structure, for example tab 23 of shell 12 as shown, and a user's face, to thereby enforce a predeterminable, limited deformation of seal member 18 which may be imposed upon application of the mask to a user's face. Specifically, and with reference to FIGS. 2 and 3, there is shown a spacer block in the form of a generally trapezoidal body 56 having a pressure sensitive adhesive strip 58 by which it may be selectively secured to the face mask 10 such as by being secured to the upper strap receiving tab 23 as shown in FIG. 2. The spacer element may be of any suitable material consistent with the objectives of light weight, economy, and user comfort. For example, a spacer element of foam rubber may be suitable, given that the foam rubber material is of sufficient resilience and stiffness to define a distinct standoff distance between the mask and the user's face without presenting any surfaces so hard that they would produce discomfort in contact with the user's face. From this, it will be appreciated that the spacer blocks may also be of laminated or laid-up construction, or a variety of other known structures consistent with the stated objectives. FIG. 6 illustrates one spacer embodiment in the form of a family of spacer block elements of different sizes, wherein spacing adjustment is achieved by substituting one such spacer block for another. Alternatively, the family of spacers may be provided by one or more unitary spacer elements, each having a plurality of spacing portions as shown in FIG. 7 for example, wherein spacing dimension $S_1$ differs from spacing dimension $S_2$.

In use as described, the one of the family of spacer blocks which provides the proper standoff or spacing is applied to the mask 10 as shown and the mask then applied to the user's face with the spacer 56 defining the limit of deformation for seal member 18 adjacent the upper portions thereof. A system of straps such a suitable head harness arrangement (not shown) is then utilized to retain the mask adjacent the user's face that the proper standoff distance, the lower straps being passed through apertures 22 in tabs 24 and being tightened just sufficiently to deform the seal member 18, with the upper portion thereof at the prescribed standoff distance, into sealing engagement with the user's face. Judicious selection of the proper spacer, in conjunction with proper tensioning of the harness straps, affords a mask fit which gives optimal seal performance with minimal force or pressure of the seal against the user's face.

Of course, any of a variety of alternative spacer embodiments may be employed in lieu of the described family of spacer blocks. For example, an adjustable screw spacer or an inflatable balloon-like spacer may be mounted with respect to the mask structure in a manner such as described above for spacer 56. Furthermore, the stiffness of the described spacer blocks 56 in resilient deformation preferably is greater than the stiffness of the described seal.

The invention having thus been described with reference to particular presently preferred embodiments thereof, it will be appreciated that I have contemplated various alternative and modified embodiments. Of course, many such alternatives and modifications would also occur to others versed in the art, once apprised of my invention. Accordingly, it is intended that the invention be construed broadly and limited only by the scope of the claims appended hereto.

I claim:

1. In a respiratory mask adapted to receive breathing gas from a gas supply means and further adapted for confronting engagement with the face of a human user to facilitate administration of such breathing gas to such a user, the combination comprising:
    a mask body adapted to carry a flexible seal means;
    a flexible seal means affixed to said mask body and adapted for such confronting engagement with such a user's face to form an annular sealed interface encompassing a predetermined portion of such user's face;
    said seal means including a flexible peripheral sidewall portion which projects from of said mask body and a seal portion formed adjacent an outer extent of said sidewall portion and spaced from said mask body; and
    means to limit deformation of said seal means when in engagement with a user's face, said means to limit including spacer means affixed to said mask body and cooperable therewith to limit the approach of said mask body toward the face of such a user.

2. The combination as claimed in claim 1 additionally including a support means closely encompassing substantially the entire extent of said sidewall portion and coextending therewith from said mask body to an extent less than said outer extent.

3. The combination as claimed in claim 2 wherein said support means is cooperable with said seal means to limit deformation of said sidewall portion.

4. The combination as claimed in claim 3 wherein said support means is cooperable with said seal means to limit deformation of said sidewall portion to differing magnitudes of deformation at differing locations about the periphery of said seal means.

5. The combination as claimed in claim 4 wherein said support means includes a rigid support element which coextends with said sidewall portion from said mask body, the outermost extent thereof from said mask body being generally different for selected different locations about the periphery of said seal portion.

6. The combination as claimed in claim 4 wherein said outermost extent of said support element includes a contoured outer peripheral edge of said support element which extends about the periphery of said seal means.

7. The combination as claimed in claim 1 wherein said spacer means is affixed to said mask body outside of the area encompassed by said support means.

8. The combination as claimed in claim 7 wherein said spacer means is adjustable to provide selectively variable standoff distance of said mask body from the face of such a user.

9. The combination as claimed in claim 8 wherein said spacer means includes a plurality of differently sized spacer block means which may be selectively applied to said mask body for cooperation therewith to selectively vary the minimum standoff distance of said mask body from the face of such a user.

10. The combination as claimed in claim 9 wherein said plurality of spacer block means includes plural spacer block portions of a unitary spacer element.

11. The combination as claimed in claim 10 wherein said seal means includes a plurality of upstanding, resiliently deformable rib means distributed internally of said sidewall portion about the internal periphery thereof and extending outwardly of said mask toward said outer extent of said sidewall portion.

12. The combination as claimed in claim 11 wherein said rib means are formed integrally with said seal means.

13. The combination as claimed in claim 12 wherein said seal portion includes a radially inturned seal flap extending from said sidewall portion so as to present a generally annular sealing surface for confronting engagement with the face of such a user.

14. In a respiration system adapted for administering breathing gas to a user, the combination comprising:
    a mask adapted to receive breathing gas from a gas supply means and further adapted to be placed in confronting engagement with the face of such a user to form a sealed interface therewith;
    said mask including a relatively flexible seal means adapted to encompass a portion of the face of such a user and a relatively inflexible mask body which carries said seal means; and
    means to limit deformation of said seal means when in engagement with a user's face;
    said means to limit including spacer means which is cooperable with said mask body in a position for confronting engagement with the face of such a user to limit the approach of said mask body toward the face of such a user.

15. The combination as claimed in claim 14 wherein said spacer means is affixed to said mask body outside of the area encompassed by said seal means.

16. The combination as claimed in claim 15 wherein said spacer means is adjustable to provide selectively variable standoff distance of said mask body from the face of such a user.

17. The combination as claimed in claim 16 wherein said spacer means includes a plurality of differently sized spacer block means which may be selectively applied to said mask body for cooperation therewith to selectively vary the minimum standoff distance of said mask body from the face of such a user.

18. The combination as claimed in claim 17 wherein said spacer block means are formed of resiliently deformable material.

19. The combination as claimed in claim 18 wherein said seal means extends outwardly of said mask body for confronting engagement with the face of such a user.

20. The combination as claimed in claim 19 wherein the stiffness of the said spacer block means in resilient deformation thereof is greater than the stiffness of said seal means.

21. The combination as claimed in claim 19 wherein said spacer means is affixed to said mask body in an orientation to extend outwardly thereof in the same direction as and to an extent less than the outward extent therefrom of said seal means.

* * * * *